United States Patent
Hale et al.

(10) Patent No.: US 8,504,511 B2
(45) Date of Patent: Aug. 6, 2013

(54) SYSTEM AND METHOD FOR PROVIDING LOCALIZATION OF RADIOLOGICAL INFORMATION UTILIZING RADIOLOGICAL DOMAIN ONTOLOGY

(75) Inventors: Charles R. Hale, Trumbull, CT (US); Yihong Ding, Westport, CT (US)

(73) Assignee: FUJIFILM Medical Systems USA, Inc., Stamford, CT (US)

(*) Notice: Subject to any disclaimer, the term of this patent is extended or adjusted under 35 U.S.C. 154(b) by 723 days.

(21) Appl. No.: 12/570,750

(22) Filed: Sep. 30, 2009

(65) Prior Publication Data

US 2011/0033095 A1 Feb. 10, 2011

Related U.S. Application Data

(63) Continuation-in-part of application No. 12/535,825, filed on Aug. 5, 2009.

(51) Int. Cl.
*G06N 5/00* (2006.01)
(52) U.S. Cl.
USPC .............................. 706/54; 706/45
(58) Field of Classification Search
USPC ...................................... 706/54, 45
See application file for complete search history.

(56) References Cited

U.S. PATENT DOCUMENTS

| | | | |
|---|---|---|---|
| 6,526,415 B2 | 2/2003 | Smith et al. | |
| 6,654,731 B1 | 11/2003 | Mahesh | |
| 7,020,326 B1 | 3/2006 | Hsu | |
| 7,136,852 B1 | 11/2006 | Sterling et al. | |
| 7,209,923 B1 | 4/2007 | Cooper | |
| 7,260,480 B1 | 8/2007 | Brown et al. | |
| 7,289,651 B2 | 10/2007 | Vining et al. | |
| 7,421,647 B2 | 9/2008 | Reiner | |
| 7,493,253 B1 | 2/2009 | Ceusters et al. | |
| 7,505,989 B2 | 3/2009 | Gardner et al. | |
| 7,512,575 B2 | 3/2009 | Mahesh | |
| 7,512,576 B1 | 3/2009 | Syeda-Mahmood et al. | |

(Continued)

FOREIGN PATENT DOCUMENTS

| | | |
|---|---|---|
| JP | 11066197 | 3/1999 |
| JP | 2001118008 | 4/2001 |

(Continued)

OTHER PUBLICATIONS

Wennerberg, et al., Kemm: A Knowledge Engineering Methodology in the Medical Domain, Proc of the 5th International Conference on Formal Ontology in Information Systems (FOIS). Saarbruecken, Germany, Jun. 19, 2008, pp. 1-13.*

(Continued)

*Primary Examiner* — Wilbert L Starks
(74) *Attorney, Agent, or Firm* — Woods Oviatt Gilman LLP

(57) ABSTRACT

The present invention is directed in general to a system and method that employs radiological localization ontology to localize specified and modeled radiological domain knowledge. A system and method are provided that allows for consulting the ontology in the context of the model the ontology fulfills. The result of consulting the ontology will be localized radiological information based on information provided in the consultation. Even further, such result is validated, identified and classified radiological information that is based on information provided in the consultation. By consulting the ontology the system is also able to translate designated radiological information from one localized representation to another and consult a language independent radiological domain knowledge.

11 Claims, 6 Drawing Sheets

U.S. PATENT DOCUMENTS

| | | | |
|---|---|---|---|
| 7,542,969 B1 | 6/2009 | Rappaport et al. | |
| 7,908,293 B2 | 3/2011 | Aronson et al. | |
| 8,046,226 B2 | 10/2011 | Soble et al. | |
| 2002/0046062 A1 | 4/2002 | Kameda | |
| 2004/0125131 A1 | 7/2004 | Phelps | |
| 2005/0170323 A1 | 8/2005 | Jarrell et al. | |
| 2005/0182657 A1 | 8/2005 | Abraham-Fuchs et al. | |
| 2006/0100738 A1 | 5/2006 | Alsafadi et al. | |
| 2006/0143046 A1 | 6/2006 | Kawakami et al. | |
| 2006/0265249 A1 | 11/2006 | Follis et al. | |
| 2006/0271556 A1 | 11/2006 | Mukherjee et al. | |
| 2007/0005621 A1 | 1/2007 | Lesh et al. | |
| 2007/0027636 A1 | 2/2007 | Rabinowitz | |
| 2007/0055552 A1 | 3/2007 | St. Clair et al. | |
| 2007/0094188 A1 | 4/2007 | Pandya et al. | |
| 2007/0198250 A1 | 8/2007 | Mardini | |
| 2008/0027889 A1 | 1/2008 | Zhou et al. | |
| 2008/0037852 A1 | 2/2008 | Zhou et al. | |
| 2008/0052126 A1 | 2/2008 | Sasai et al. | |
| 2008/0059391 A1 | 3/2008 | Rosales et al. | |
| 2008/0201172 A1 | 8/2008 | McNamar | |
| 2008/0201280 A1 | 8/2008 | Martin et al. | |
| 2008/0208631 A1 | 8/2008 | Morita et al. | |
| 2008/0243548 A1 | 10/2008 | Cafer | |
| 2008/0244453 A1 | 10/2008 | Cafer | |
| 2008/0270120 A1 | 10/2008 | Pestian et al. | |
| 2008/0294459 A1 | 11/2008 | Angell et al. | |
| 2008/0312961 A1 | 12/2008 | Alsafadi | |
| 2009/0006467 A1 | 1/2009 | Visscher | |
| 2009/0018867 A1 | 1/2009 | Reiner | |
| 2009/0030731 A1 | 1/2009 | Reiner | |
| 2009/0037220 A1 | 2/2009 | Chambers et al. | |
| 2009/0055378 A1 | 2/2009 | Alecu et al. | |
| 2009/0076839 A1 | 3/2009 | Abraham-Fuchs et al. | |
| 2009/0099862 A1 | 4/2009 | Fireman et al. | |
| 2009/0132285 A1 | 5/2009 | Jakobovits | |
| 2009/0192800 A1 | 7/2009 | Brandt | |
| 2009/0222286 A1 | 9/2009 | Elsholz | |
| 2009/0228299 A1 | 9/2009 | Kangarloo et al. | |
| 2010/0063799 A1 | 3/2010 | Jamieson | |
| 2010/0131883 A1 | 5/2010 | Linthicum et al. | |
| 2010/0138231 A1 | 6/2010 | Linthicum et al. | |
| 2010/0145720 A1 | 6/2010 | Reiner | |
| 2010/0293164 A1 | 11/2010 | Weese et al. | |

FOREIGN PATENT DOCUMENTS

| | | |
|---|---|---|
| JP | 2003122849 | 4/2003 |
| JP | 2004005565 | 1/2004 |
| JP | 2007304661 | 11/2007 |
| JP | 2008021015 | 1/2008 |
| JP | 2008192002 | 8/2008 |
| JP | 2008250747 | 10/2008 |
| JP | 2008250748 | 10/2008 |
| WO | WO 2007/024617 | 3/2007 |
| WO | WO 2008/115449 | 9/2008 |

OTHER PUBLICATIONS

Achour, et al., A UMLS-based Knowledge Acquisition Tool for Rule-based Clinical Decision Support System Development, Journal of the American Medical Informatics Association vol. 8 No. 4 Jul./Aug. 2001, pp. 351-360.*

Jannin, et al., Model for defining and reporting Reference-based Validation Protocols in Medical Image Processing, Int Journ. Comput. Assisted Radiol and Surg. 2006, pp. 1-26.*

Rubin, Daniel L, et al, "Protege: A Tool for Managing and Using Terminology in Radiology Applications," Journal of Digital Imaging, vol. 0, No. 0, 2007: pp. 1-13.

Biolchini, Jorge,"Developing a UMLS-based Ontology of Cardiology Procedures for Cognitive Support in Medical Decision Making,"Lister Hill Nat'l Ctr.,Nat'l Lib. Med., Apr. 4, 2002.

Baneyx, Audrey, et al, "Methodology to Build Medical Ontology from Textual Resources," AMIA Annu. Symp. Proc. 2006; 21-25.

Galanis, Dimitrios, et al, "An Open-Source Natural Language Generator for OWL Ontologies and its Use in Protege and Second Life," Athens University of Econ/Bus., Athens Greece.

Jackson, Jakieda R., "Non-Final Office Action," for U.S. Appl. No. 12/572,602, filed Oct. 2, 2009, mailed Dec. 23, 2011, Alexandria, Virginia.

Azad, Abul K., "Non-Final Office Action," for U.S. Appl. No. 12/625,880, filed Nov. 25, 2009, mailed Sep. 28, 2012, Alexandria, Virginia.

Winston III, Edward B., "Non-Final Office Action," for U.S. Appl. No. 12/556,923, filed Sep. 10, 2009, mailed Dec. 9, 2011, Alexandria, Virginia.

Fernandez Rivas, Omar F., "Non-Final Office Action," for U.S. Appl. No. 12/587,174, filed Oct. 2, 2009, mailed Mar. 29, 2012, Alexandria, Virginia.

Marwede et al ("RadiO: Prototype Application Ontology for Radiology Reporting Tasks" AMIA 2007).

Zhou et al ("Semantics and CBIR: A Medical Imaging Perspective" Jul. 2008).

Daniel Rubin ("Creating and Curating a Terminology for Radiology: Ontology Modeling and Analysis" 2008).

Gangemi Et Ak ("Modeling Ontology Evaluation and Validation" 2006).

Wong, Lut, "Non-Final Office Action," for U.S. Appl. No. 12/535,825, filed Aug. 5, 2009, mailed Mar. 26, 2012, Alexandria, Virginia.

* cited by examiner

SYSTEM AND METHOD FOR PROVIDING LOCALIZATION OF RADIOLOGICAL INFORMATION UTILIZING RADIOLOGICAL DOMAIN ONTOLOGY

CROSS REFERENCE TO RELATED APPLICATIONS

This application is a continuation-in-part of prior U.S. patent application Ser. No. 12/535,825, filed Aug. 5, 2009. The content of U.S. patent application Ser. No. 12/535,825 is hereby incorporated by reference in its entirety.

TECHNICAL FIELD

The present invention is directed in general to localization of a computing environment in medical imaging and Picture Archiving and Communication Systems (PACS). A system and method are provided that allow for consulting radiological localization ontology in the context of the model the ontology fulfills. The result of consulting the ontology will be localized radiological information based on information provided in the consultation. By consulting the ontology, the system is also able to translate designated radiological information from one localized representation to another. Users are able to interact in multiple languages, dialects and paradigms with underlying radiological domain ontology.

BACKGROUND OF THE INVENTION

In the medical arena, a plethora of computing environments and systems are engaged for the acquisition, storage, retrieval, presentation and distribution of a myriad of information relating to patients, procedures, administrative tasks, etc. An example of such a system in the imaging field might be a Picture Archiving and Communication Systems (PACS). PACS are a combination of computers and/or networks dedicated to the storage, retrieval, presentation and distribution of images. While images may be stored in a variety of formats, the most common format for image storage within the PACS system is Digital Imaging and Communications in Medicine (DICOM). DICOM is a standard in which radiographic images and associated meta-data are communicated to the PACS system from imaging modalities for interaction by end-user medical personnel.

Medical personnel spend a significant amount of their time addressing administrative tasks. Such tasks include, for example, documenting patient interaction and treatment plans, preparing billing, reviewing lab results, recording observations and preparing reports for health insurance. Time spent on performing such tasks diminish the time available for patients and in some instances lead to inaccurate and hastily compiled reports or records when personnel are faced with the need to see multiple patients.

In order to address time deficiency issues, the current trend in the medical field is to automate as many health care related processes as possible by leveraging various technologies, and thereby freeing up personnel to spend more time with patients rather than performing administrative tasks. Another objective in this arena is to ensure that administrative tasks are accomplished in an accurate and consistent manner. One approach to achieving this objective is to provide a standardized representation for healthcare related data, particularly within the various specialty areas, such as radiology, cardiology, etc.

Health care data is not easily reusable by disparate groups in the radiological field because it is stored with different methods and in different formats across a wide range of information technology. Various initiatives by groups and organizations across the globe, including the National Institutes of Health, Food and Drug Administration, and other medical bodies, have driven a set of standards for the consolidation of medical information into a common framework. One such standard is RadLex, which is a standard radiological lexicon proposed by the Radiological Society of North America, for uniform indexing and retrieval of radiology information. RadLex is a taxonomy having class hierarchies. RadLex functions essentially as a dictionary of terms and the relationships among the terms. RadLex has some crucial limitations. The most significant of these limitations being the inability to support radiological findings and the relationships between findings and characteristics of the findings. What is needed is an extension to RadLex—an extension that provides domain specific modeling, which can then be applied to or utilized by a wide variety of applications such as, report tools, treatment analysis programs, tools for classification and verification of radiological information, and systems for improving radiological work flow. Such an extension would utilize an ontology that is domain specific in order to process radiological information.

The problems described above and the proposed solutions are not unique to just the United States or any other country or locale. Hence, another problem that arises in the context of existing solutions is the inability to provide accurate and efficient localization of solutions without the duplication of the entire environment. This problem is more pronounced when dealing with solutions that employ a domain ontology.

Ontology is a data model for the modeling of concepts and the relationships between a set of concepts. Ontologies are utilized to illustrate the interaction between the set of concepts and corresponding relationships within a specific domain of interest. Thus, the concepts and the relationships between the concepts can be represented in readable text, wherein descriptions are provided to describe the concepts within a specific domain and the relationship axioms that constrain the interpretation of the domain specific concepts.

Numerous current products and research efforts offer tools that streamline data integration. These products include centralized database projects such as the Functional Magnetic Resonance Imaging Data Center and the Protein Data Bank, distributed data collaboration networks such as the Biomedical Informatics Research Network, commercial tools for data organization, and systems for aggregating healthcare information such as Oracle Healthcare Transaction Base. In addition, tools have been developed to automatically validate data integrated into a common framework. Validation calls for techniques such as declarative interfaces between the ontology and the data source and Bayesian reasoning to incorporate prior expert knowledge about the reliability of each source Automated data integration and validation require fewer human resources, but necessitates that data have well-defined a priori structure and meaning. The most successful approaches make use of a standardized master ontology that provides a framework to organize input data, as well as a technology scheme for augmenting and updating the existing ontology. This paradigm has been successfully applied in various ontologies including Biodynamic Ontology, Gene Ontology, Mouse Gene Database, and the Mouse Gene projects, which provide a taxonomy of concepts and their attributes for annotating gene products. The Unified Medical Language System (UMLS) Metathesaurus and Semantic Network, combine multiple emerging standards to provide a standardized ontology of medical terms and their relationships Ontology is a philosophy of what exists. In computer science, ontology is used to model entities of the real world and the relations between them to create common dictionaries for their discussion. Basic concepts of ontology include (1) classes of instances/things, and (2) relations between the classes, as described herein below. Ontology provides a vocabulary for talking about things that exist.

Relations, also referred to as properties, attributes and functions are specific associations of things with other things. Relations can include:

Relations between things that are part of each other, e.g., between a car and its tires;

Relations between things that are related through a process such as the process of creating the things, e.g., a painter and his/her painting; and Relations between things and their measures, e.g., a tumorous mass and its size.

Some relations also associate things to fundamental concepts such as size, which would be related to large or small, or morphology which would be related to the shape of a mass such as round or linear.

Relations play a dual role in ontology. In one instance, individual things are referenced by way of properties, e.g., a person by a name or characteristic, or music by its title and composer. In another instance, knowledge being shared is often a property of things too. A thing can be specified by some of its properties, in order to query for the values of its other properties.

Not all relations are relevant to all things. It is convenient to discuss the domain of a relation as a "class" of things, also referred to as a category. Often domains of several relations may coincide.

There is flexibility in the granularity to which classes are defined. Assume automobile is a class. Ford cars may also be a class, with a restricted value of a brand property. However, this would only be a logical definition if Ford cars had attributes that were of interest or common to other automobiles. Generally, one can define classes as granular as an individual automobile unit, although an objective of ontology is to define classes that have important attributes.

There are a number of functionalities not provided by the systems described earlier. Accordingly, there is a need for a comprehensive system which is capable of enabling researchers to: 1) efficiently enter heterogeneous local data into the framework of the Unified Medical Language System (UMLS)—based ontology, 2) make necessary extensions to the standardized ontology to accommodate their local data, 3) validate the integrated data using expert rules and statistical models defined on data classes of the standardized ontology, 4) efficiently upgrade data that fails validation, and 5) leverage the integrated data for clinical outcome predictions. This is particularly the case in the field of radiology, and even more specifically within the various domains therein such as mammography.

To overcome some of the deficiencies earlier described, some existing systems have attempted to minimize the amount of effort that may be required to report on radiological findings. However, these systems suffer from a myriad of drawbacks. Essentially these solutions have: a non-standard library or vocabulary; no error, terminology or consistency checking; no collaboration or tool that can be used by other application programs, and issues relating to language, more specifically localization. It would be both cumbersome and unwieldy to duplicate systems for different localization environments or languages.

The shortcomings of the prior art are overcome and additional advantages are provided through the provision of a method for utilizing localized ontology that can consult other base ontology. The base ontology being based upon data obtained from unstructured and semi-structured knowledge sources to provide identification, validation and classification of localized radiological concepts.

The present invention addresses these needs as well as other needs.

SUMMARY OF THE INVENTION

The present invention is directed in general to a system and method that employs radiological localization ontology and radiological domain ontology to specify and model localized radiological information as knowledge. The present invention provides a methodology to consult the domain ontology and provide information in reference to a subject via the localization ontology. The consultation facilitates reporting on images that may be specific to one modality or more than one modality. The method comprises defining one or more aspects of radiology functions as concept properties represented by a vocabulary of one or more instances of the radiological domain ontology.

Radiological localization ontology fulfills a model of radiological domain knowledge by employing a context that defines a set of domain knowledge and the relationships among said set of domain knowledge with respect to imaging modalities when necessary or appropriate. In other words, this ontology can contain information that is non-modality specific. The invention validates that a localized information item of interest relating to a subject or imaging modality, is radiological in nature and resides in the domain knowledge. The invention further identifies a definitive concept of said localized information item from within said domain of knowledge and classifies the information item as a finding or finding characteristic that has object properties. The object properties represent relationships among said findings and finding characteristics.

An ontological system and method are presented that allow for consulting radiological domain ontology for information including:
  a. Connecting to specific radiological domain model ontology in a specific language and dialect.
  b. Connecting to specific radiological domain model ontology in multiple languages each with a specific dialect.
  c. Translating between languages for specific radiological domain ontology.

Exemplary embodiments of the present invention relate to a solution for the extraction of information from unstructured knowledge sources of radiological report information and non-radiological knowledge sources, for example clinical information, patient history or clinical/surgical consultation. Further, ontological relationships are inferred between the extracted information. The inferred ontological relationships are identified, verified and classified for any number of localization environments.

BRIEF DESCRIPTION OF THE DRAWINGS

The above-mentioned features and other features and advantages of this invention, and the manner of attaining them, will become apparent and be better understood by reference to the following description of the invention in conjunction with the accompanying drawings, wherein.

DETAILED DESCRIPTION OF THE INVENTION

Figure 1:
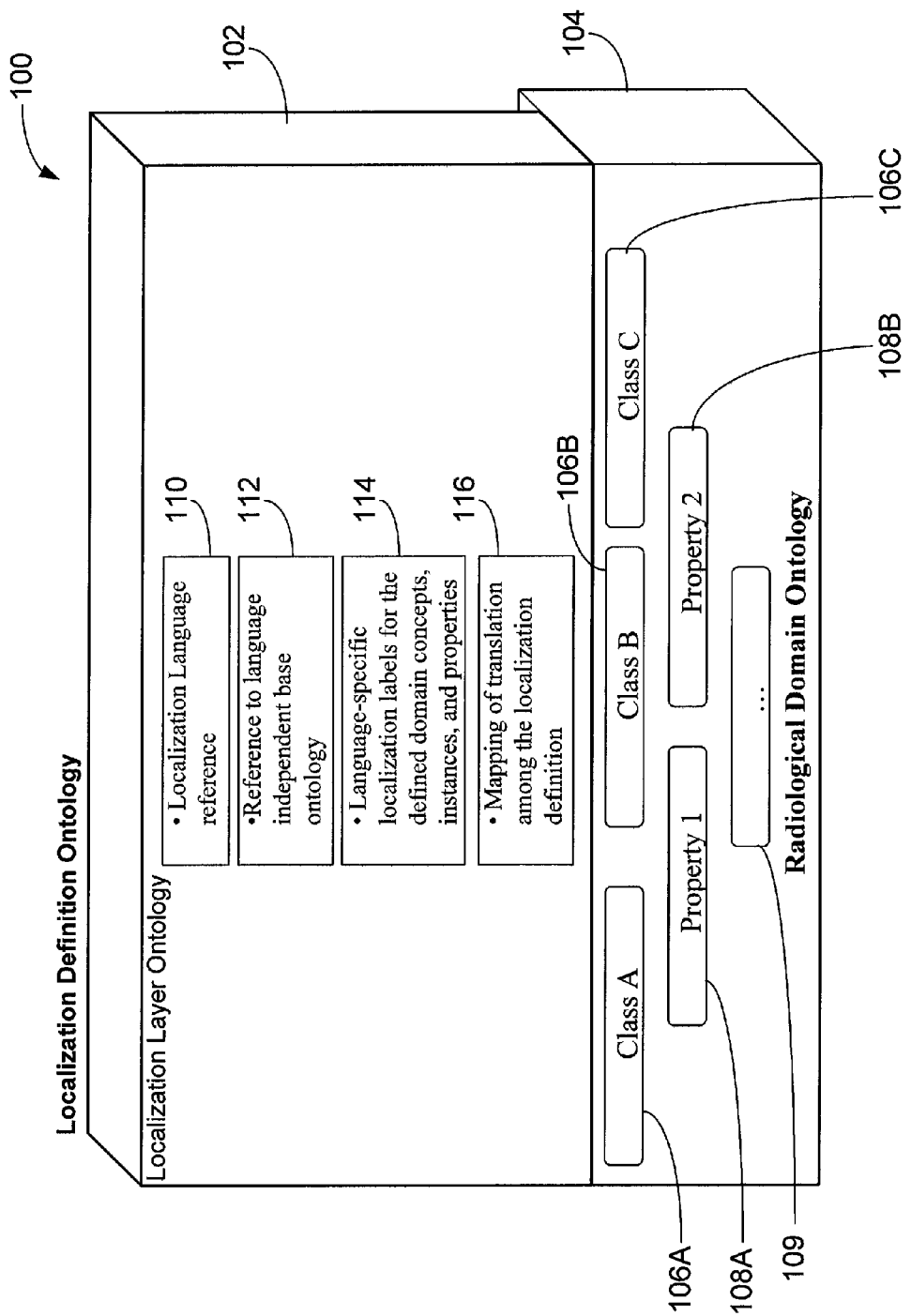
FIG. 1 is an illustrative block diagram of a localization definition ontology comprising a localization layer ontology and a radiological domain ontology for declaring and fulfilling a model of radiological domain knowledge according to the present invention.

Generally, the system and methods described herein may be implemented in hardware, software or a combination thereof. The disclosed embodiments are intended to be illustrative since numerous modifications and variations thereof will be apparent to those of ordinary skill in the art.

This document is organized as follows. In the first section, an overview of the techniques and implementation necessary to provide localized consistency of terminology in radiological consulting and reporting in accordance with the present invention are provided and described. In the next section, an exemplary implementation of particular features of the present invention for localizing radiological domain knowledge is discussed. Following this, other aspects of the invention as they pertain to use and function of the invention are discussed. Finally, an exemplary computer environment for the implementation and use of the invention is described.

The present invention is directed in general to a system and method that employs radiological localization ontology to specify and model localized radiological information as knowledge. A system and method are provided that allow for consulting radiological localization ontology in the context of the model the ontology fulfills. The result of consulting the ontology will be localized radiological information based on information provided in the consultation. Such localized information is identified, validated and classified as radiological information by the system of the present invention.

In one aspect, the present invention provides a system and method for modularizing and layering localization. A base domain ontology may be transparently provided beneath a localization layer ontology, thus minimizing the number and aspects of the system components that may need to be changed for each localization implementation or environment.

In another aspect, the present invention provides a system and method for translating radiological information between a plurality of localization environments such as languages, dialects, etc.

In a further aspect, the present invention provides a solution for the extraction of localized information from an unstructured knowledge source. A set of subject-matter specific relationships are established as a logical foundation for the ontological subject matter domain. The subject-matter specific relationships can be derived partially from a pre-existing information source (e.g., RadLex, the radiological lexicon) and partially from the knowledge that needs to be modeled for an identified subject. For example, ontology on the subject of mammography will use lumps or masses as topic concepts. The relationships may correspond to disease-specific relationships such as biopsy, additional exam, symptoms, location, further treatments, etc. Once the subject-matter specific relationships have been established, the unstructured/non-radiological knowledge sources are parsed in order to identify topic headings and content texts that are associated with respective topic headings within the knowledge source. The context texts that are identified within the unstructured knowledge source correspond to the predetermined subject-matter specific relationship. It should be understood that the source of the unstructured information is varied and includes such sources as spoken words, a user's typing, reports, systems or applications that need to determine if a piece of information is radiological.

The textual content (finding) is then analyzed to identify references to concepts—wherein concept reference descriptors (finding characteristics) can be obtained and presented to a system user or to other down-line applications or systems. For each concept reference descriptor that is identified, an analysis is performed of relevant textual content information to identify references to concept descriptors that exist within the textual content information.

The present invention utilizes ontology to define a set of knowledge and relationships among the knowledge thereby employing a context. For example, if there is a finding of a tumorous mass in an image, the system knows what other information would be relevant to that finding such as size, density, location and other characteristics that apply to that finding, as well as the relationships between the findings and finding characteristics. The present invention also utilizes ontology to define localization of said knowledge and the relationships among the knowledge.

Ontological models are used to talk about "things." An important vocabulary tool is "relations" between things. An ontology model itself does not include the "things," but introduces classes and relations, which can then be used as a vocabulary for talking about and classifying things. In the field of medicine, ontology is used in solving problems in the field of medical terminology, including the organization of copious amounts of data, the alignment and integration of heterogeneous knowledge, and disambiguates in terminology.

The present invention provides a combination of an intelligent database and system, which can provide not only stored information but also information which can be determined by knowledge of the technical domain.

In an embodiment of the present invention, the radiological domain ontology is constructed using combinations of one or more of the following World Wide Web Consortium standards:

RDF—Resource Description Framework
RDFS—RDF Schema
OWLDL—Web Ontology Language Description Logic version Although the following discussions and the present invention are described in relation to a biological imaging system, it should be understood that the invention is also applicable to other information/imaging technologies, systems or text reports.

Imaging systems as discussed herein, include those wherein image manipulation, image attributes, and features of an imaging system are required to be intuitively and easily analyzed and/or reported, including non-medical systems, visual analysis and diagnostic tools, and other visual user interface environments. Further, the present invention is described with reference to mammography and particular imaging modalities. However, the system and method of the present invention is equally applicable to other radiological domains and imaging modalities. The use of the present invention in and by other applications or by other systems or tools are anticipated and within the scope of the present invention. Further still, various operations, functions, modeling and definitions, while described as being present within the radiological domain ontology or the localization layer ontology, may well belong one in the other or be split across both environments. Generally, all reference to ontology should be considered to be a reference to an all encompassing localization definition ontology 100 as shown in FIG. 1.

An ontology on the subject of radiology in general or mammography specifically, may use findings and finding characteristics as topic concepts while the relationships may correspond to disease-specific relationships. In an embodiment of the present invention, a localization definition ontology 100 that both declares and fulfills a model of localized radiological domain knowledge may be described as shown in FIG. 1.

Referring initially to FIG. 1, pathological, physiological and iatrogenic entities and pathological, physiological and iatrogenic observations may be modeled conceptually as radiological concepts. Concepts, concept instances or properties may be expressed by a vocabulary that is defined in a radiological domain as radiological knowledge. Therefore, in connection with a particular image that is being observed or considered by a radiologist, various aspects of the image may be described by expressions. The expressions are modeled as labels with language tags for an instance of the concept to which the expressions apply. The expressions may also be modeled as data type properties with language tags for an instance of the concept to which the expressions apply. The expressions may also be modeled under separate, independent classes that are connected to the respective domain definitions through object properties.

As shown in FIG. 1, localization definition ontology 100 may comprise a localization layer ontology 102 and a radiological domain ontology 104. In an embodiment of the present invention, the radiological domain ontology 104 is language independent and is provided as a base ontology. The radiological domain ontology 104 may be defined by classes (concepts) 106A, 106B, 106C, properties 108A, 108B and other objects 109. As previously mentioned, the concepts 106A, 106B, 106C, properties 108A, 108B and other objects 109 would therefore represent a radiological knowledge domain, which could be used to describe informational items that pertain to a patient, image, etc.

The localization layer ontology 102 may be characterized by: localization language reference 110; language independent base radiological domain ontology reference 112; language specific localization labels 114; and localization definition translation mappings 116. The localization language reference 110 provides, as the name suggests, a reference for the one of more languages that is intended to be supported for a given implementation of the invention. The language independent base ontology reference 112 provides an association/correlation of terms from a localization language to the terms of the base radiological domain ontology 104. Language-specific localization labels 114 are one or more direct translations or equivalent translations for the concepts 106, properties 108 and instances of the base radiological domain ontology 104. The translation mappings 116 provide a mapping of at least one localization default term in one language to a localization default term in another language. In some instances there may be a mapping of more than one label when a term or word in a first language may be represented by multiple terms/words in a second language. In other words, the mapping recognizes and addresses the fact that most languages may not have a direct one to one translation of vocabulary terms. The modeled radiological domain ontology 104 may further contain constraints on radiological findings, radiological finding characteristics, and relationships. Further still, the base radiological domain ontology 104 may also contain concept properties, such as applicability to a user interface or application localization, i.e., language indication.

In operation, the localization layer ontology 102 may be consulted with a localized informational item of interest, which may need to be validated, identified, and/or classified. A mapping of the localized informational item to the defined concepts 106A, 106B, 106C, properties 108A, 108B and instances of the base radiological domain ontology 104 is provided to enable a definition or characterization of the localized information item in the context of the radiological knowledge of the base radiological domain ontology 104. In other words, the base radiological domain ontology 104 may be utilized to validate, identify, and classify terms that originate in a language that is different from the language of the terms that define knowledge domain of the base radiological domain ontology 104. The steps of this process are best described and understood with reference to FIG. 2 and the object group 200.

Figure 2:
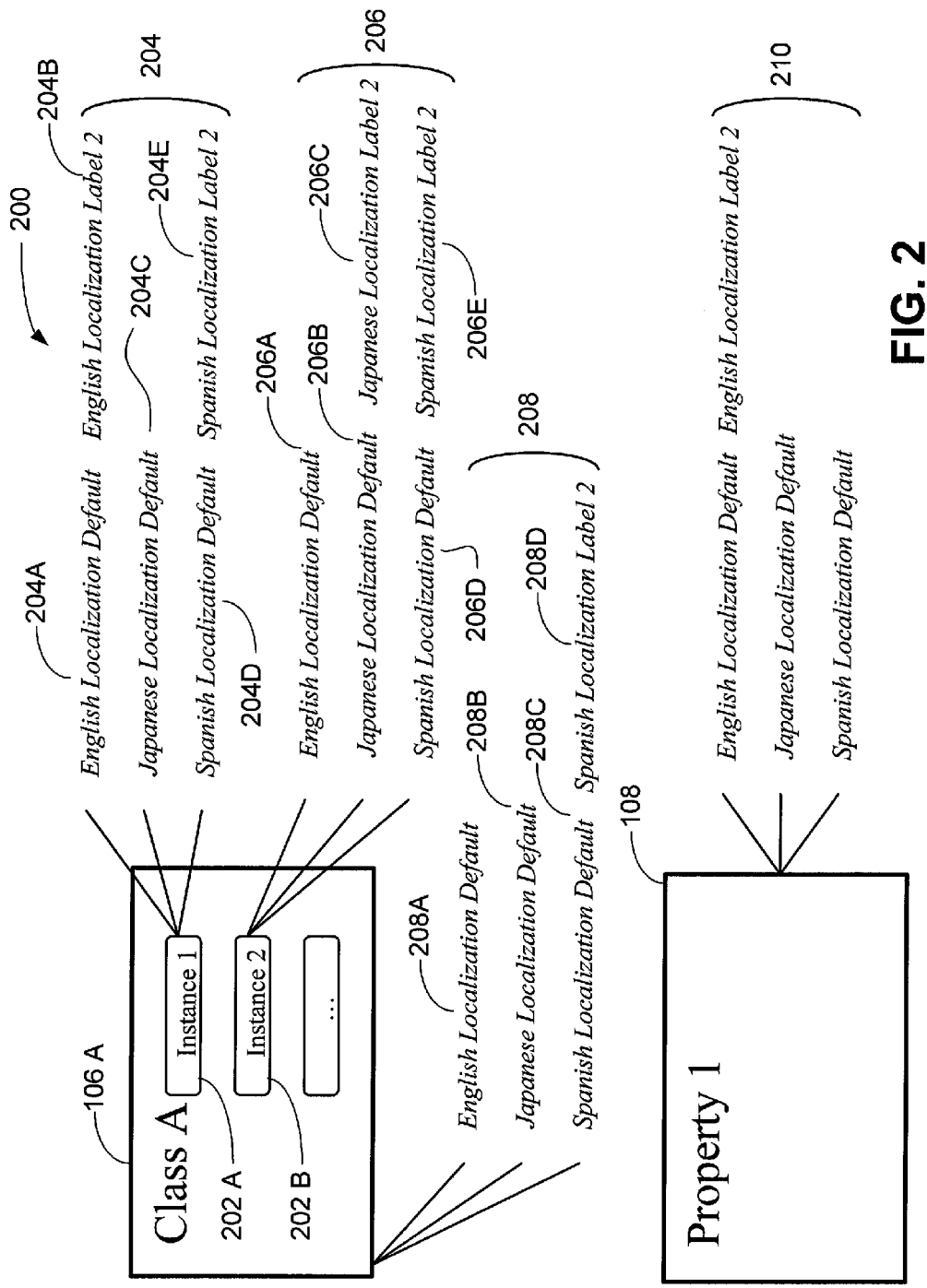
FIG. 2 is an illustrative diagram of localized labeling of classes, instances and properties of ontology concepts that represent a vocabulary for expressing the concepts of the domain definition ontology of FIG. 1.

As shown in FIG. 2, a concept such as class A 106A may include derived instances 202A, 202B. The instances 202A, 202B may further represent or further describe a finding or finding characteristic as described earlier. In accordance with an embodiment of the present invention, each of the objects within class A 106a, i.e., instances 202A, 202B, including the class A 106A itself, are modeled as labels with language tags. The language tags provide localization labels for each of the objects. Importantly, for each language or localization representation that is to be supported by the system, a minimum of one default label is provided and specified for each object. Additional labels may also be provided for any one or more of the object group 200.

For example, as shown in FIG. 2, the described embodiment of the present invention is configured to provide localization for English, Japanese and Spanish. Accordingly, instance 1 202A has a label group 204 associated with it. The label group 204 comprises at least one default label in each localization environment/language. Specifically, for the English language there is an English Localization Default 204A and an English Localization Label 204B. For Japanese there is only a Japanese Localization Default 204C. For Spanish there is a Spanish Localization Default 204D and a Spanish Localization Label 204E. Similarly, instance 2 202B has a label group 206 associated with it. Group 206 for the English language comprises an English Localization Default 206A. For the Japanese language there is a Japanese localization default 206B and a Japanese Localization Label 2 206C. For the Spanish language there is a Spanish Localization Default 206D and a Spanish Localization Label 2 206E. The Class A 106A is also tagged with a label for each supported localization, i.e., English Localization Default 208A, Japanese Localization Default 208B, Spanish Localization Default 208C and Spanish Localization Label 2 208D. Property 1 108 is also tagged with appropriate labels as represented by label group 210.

These language labels of concepts, instances and properties can be utilized as the vocabulary for describing findings in the relevant language/localization environment. Even further, the language labels provide a vocabulary guide in the sense that a radiologist can pick only one of the provided descriptions from within each of the relevant instances. As such, an individual radiologist or system utilizing the ontology cannot describe a particular finding in an inconsistent manner. For example, a mass could not be described as being both linear and round, or the size of a mass as being both large and small. The system thereby incorporates error, terminology and consistency checking.

Figure 3:
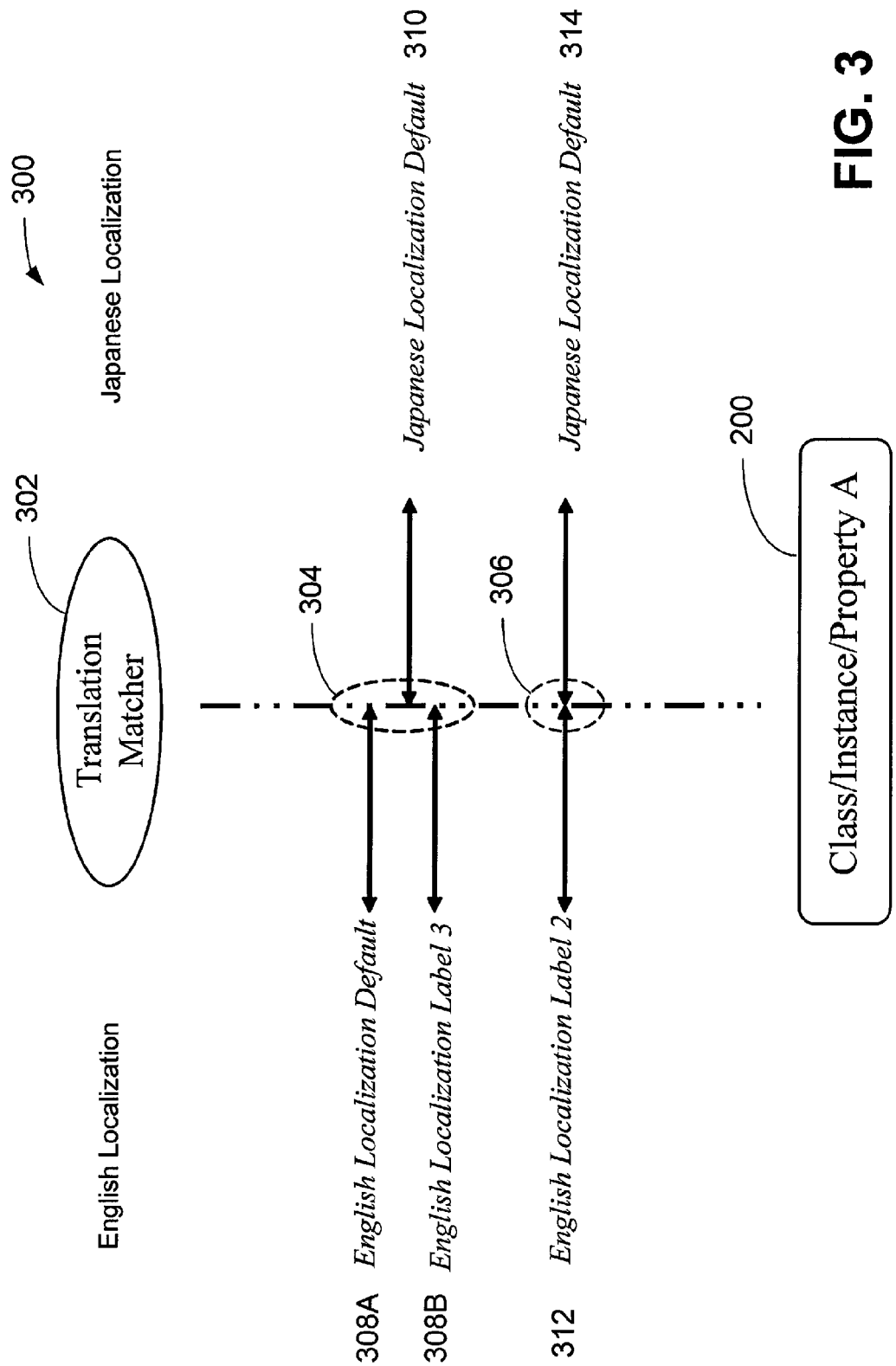
FIG. 3 is an illustrative diagram of an exemplary translation matcher for providing correlation among a plurality of localization labels and an associated class, instance and property in the domain knowledge.

In another aspect of the present invention, translation between different localizations can be provided. FIG. 3 illustrates an exemplary translation matcher for providing correlation among a plurality of localization labels and the associated class, instance and property in a knowledge domain. In the illustrated embodiment of the present invention, a translation matcher 302, provides correlation between English Localization and Japanese Localization. In operation, localization labels that were previously provided for a given domain knowledge item, i.e., class, instance or property, are mapped between localizations. For example, and as shown in FIG. 3, a particular object group 200 in the knowledge domain, may have associated therewith specific localization labels for each constituent object 304, 306. The first object 304 may have an English Localization Default 308A, and an English Localization Label 3 308B. The same first object 304 may also have Japanese Localization default 310. The translation matcher 302 provides in a pairing for the object 304, a mapping of English localization default 308A and English localization label 308B to the Japanese Localization Default 310. As previously stated, there is not always a one-to-one correlation of terms or vocabulary between languages. The translation matcher 302 provides a means to overcome this issue.

In operation, an informational item is provided to the translation matcher 302 in the English language. If the informational item matches English localization labels 308A or 308B, then that informational item may be presented in the Japanese language as Japanese localization default 310. Additionally, when an English speaker or Japanese speaker utilizes their respective localized labels 308A, 308B or 310, the provided information is translated and interpreted such that the underlying base ontology handles the consultation in an identical manner. As described herein and shown, there is essentially a two-to-one mapping from English localization to Japanese localization for the constituent object 304.

The second constituent object 306, may have an English localization label 2 312 and a Japanese localization default 314. In this case there is simply a one-to-one mapping provided by the translation matcher 302. This can be stated as follows: a one-to-one mapping from English localization to Japanese localization for constituent object 306.

As previously set forth, while the localization references are made respecting languages, it should be understood that the present invention is not limited to just language representations. Rather the present invention is directed to localization representations, meaning languages, dialects, and other adaptations for non-native environments including nations and cultures.

To facilitate reference or reporting of image related observations about a subject patient, common reference and identification of the parts of the image are necessary. The present invention provides a system and method for consulting the localization definition ontology 100 for validation, identification and classification in any of a variety of support localizations.

Figure 4:
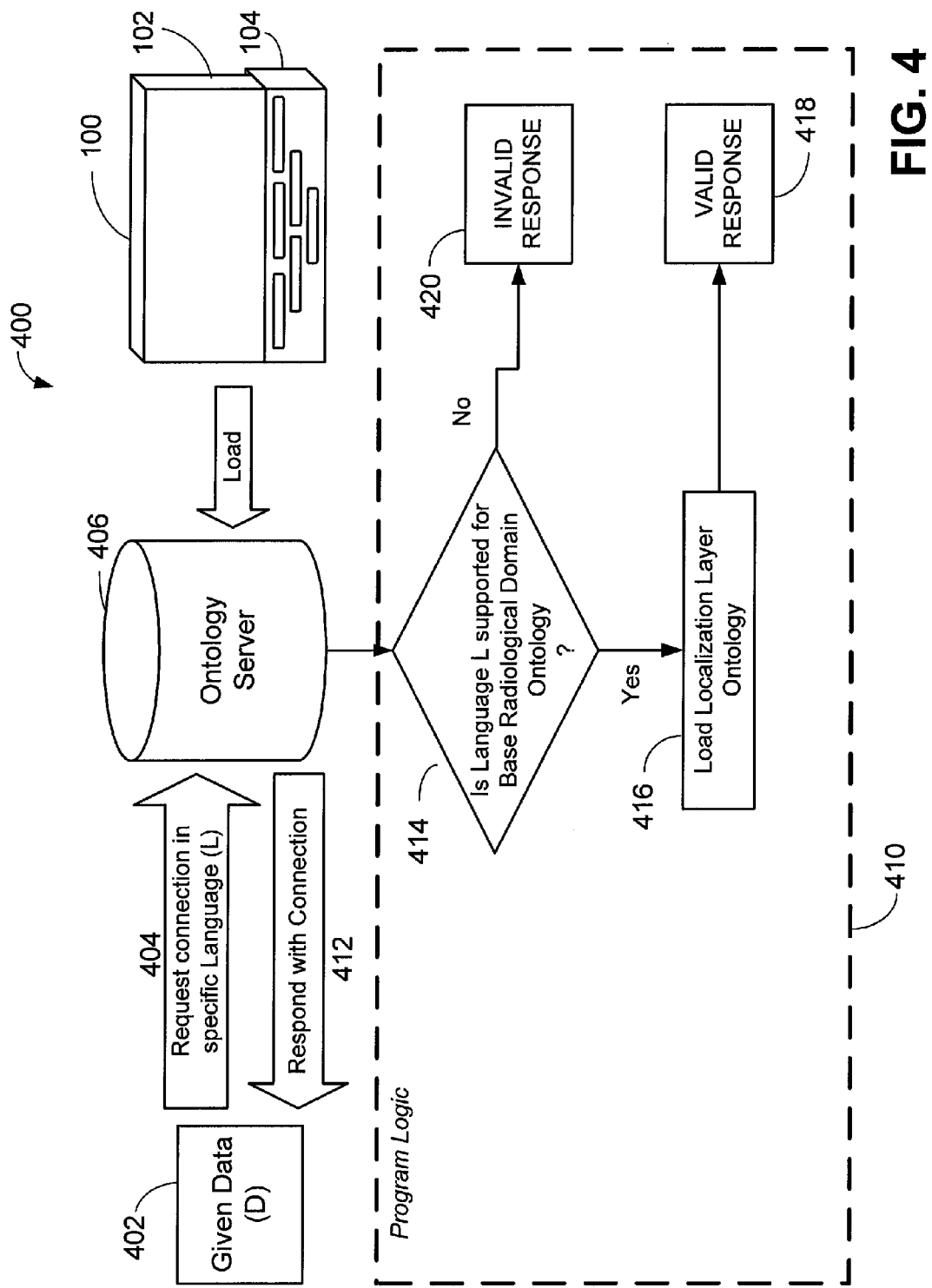
FIG. 4 is a data and flow diagram of an exemplary process for connecting to specific radiological domain model ontology in a specific language and dialect.

For example, and as illustrated in FIG. 4, an application program or other source having a given data D 402, initiates a request connection 404 in a specific one or more languages L, to an ontology server 406. The ontology server 406 is loaded with the localization definition ontology 100. As previously described, localization definition ontology 100 comprises the localization layer ontology 102 and the base radiological domain ontology 104. Program logic 412 may reside on the ontology server 406 or reside on another device having access to the ontology server 406. Program logic 410 accepts the connection request 404 and provides a connection response 412. In operation, program logic 410 determines at step 414, if the requested one or more connection Languages L are supported by the localization definition ontology 100. For each Language L that is supported, the localization layer ontology 102 for the language L is loaded at step 416. A valid response indication 418 is then provided in the connection response 412. The base radiological domain ontology 104 may be automatically loaded following, prior to or contemporaneously with step 416. Identification of a definitive concept that resides in the domain is thus determined. Classification of the given data D 402 as a finding or a finding characteristic within the domain is also determined.

In the event that the language of the given data D 402 is not supported by the localization definition ontology 100, as determined at step 414, an invalid response indication 420 is provided in the connect response 412.

Figure 5:
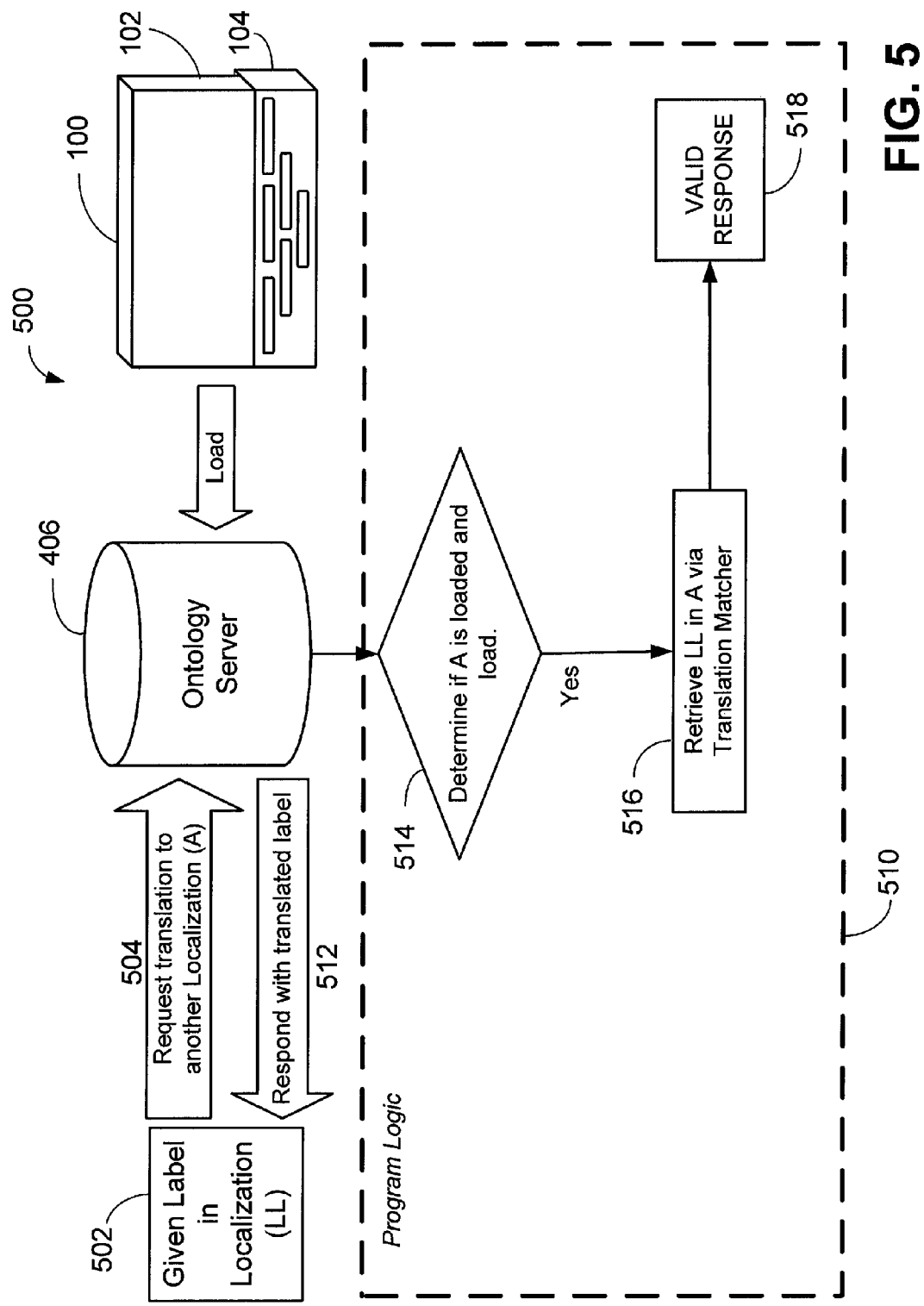
FIG. 5 is a data and flow diagram of an exemplary process for providing translation of a label in a first localization to a label in a second localization, utilizing the present invention.

In another aspect of the present invention, and as illustrated in FIG. 5, an application program or other source having a given localization label LL 502, initiates a translation request 504 to a destination localization A. Ontology server 406 is loaded with localization definition ontology 100. As previously described, localization definition ontology 100 comprises the localization layer ontology 102 and the base radiological domain ontology 104. Program logic 510 accepts the translation request 504 and provides a translated label in response 512. In operation, program logic 510 determines at step 514, if the destination localization A is supported by the localization definition ontology 100. The language reference is loaded at this point if it was not previously loaded. At step 516, utilizing the translation matcher 302, the localization label LL is retrieved in the destination localization A. A response indication 518 is provided in the translation response 512, whereby the translated label is provided.

To further illustrate an application of the various features and aspects of the invention, an implementation example of the above described invention is described next. In this exemplary implementation a radiological domain ontology for modeling mammography is utilized.

The system and method of the present invention first models the mammography information in the manner described earlier herein. That is to say that the knowledge of the mammography ontology is modeled as findings, finding characteristics, and object properties/relationships, with constraints in the mammography. Concepts properties are then defined for the domain. The localization references, references to the base ontology, and language specific localization labels are also defined in mammography.

The second thing is to provide a system and method for consulting the ontology in the form of independent software that can be utilized by other software or applications.

Turning next to a specific process where the present invention is applicable, a third party application receives three pieces of purported mammography radiological information describing a mammography radiological finding and its mammography radiological finding characteristics in English.

Utilizing the system and methods described herein, the third party application obtains a connection to the mammography domain ontology in English. The application then consults the domain ontology about each piece of purported mammography radiological information to receive validation that it is mammography radiological information. The application also receives the identity of the information and the classification for the sought after information.

The application examines the classification of each piece of information and if one informational item is classified as a mammography radiological finding then the ontology is consulted in the context of the mammography radiological finding, and the remaining information is revalidated, i.e., determine whether the radiological finding characteristics apply to that radiological finding.

These steps result in providing English radiological information that has been validated, identified and classified in the mammography domain ontology to the third party application.

In another process where the present invention may be applicable, a third party application receives three pieces of purported mammography radiological information describing a mammography radiological finding and its mammography radiological finding characteristics in Italian.

Using the system and methods described herein, the application obtains a connection to the mammography domain ontology both in English and Italian. The application then consults the domain ontology about each piece of purported mammography radiological information to receive validation that it is mammography radiological information. The application also receives the identity of the information and the classification for the sought after information.

The mammography domain ontology is then ready to be consulted using any tools that are available for doing so. Once the information has been processed and the concepts are known, i.e., identified, validated and classified, the system and method of the present invention enables conversion of the known Italian information into the default English values for those known concepts.

Radiology, which includes a variety of imaging modalities such as X-ray, Projected X-ray and MRI, comprises a plurality of findings plus numerous characteristics. The area of mammography comprises a significant number of specific findings in addition to the applicable characteristics for those findings. The present invention, while described in the domain of mammography, is applicable to any domain ontology in the field of radiology.

Having described the system and method of the present invention and an embodiment thereof, an exemplary computer environment for implementing the described design and execution is presented next.

Figure 6:
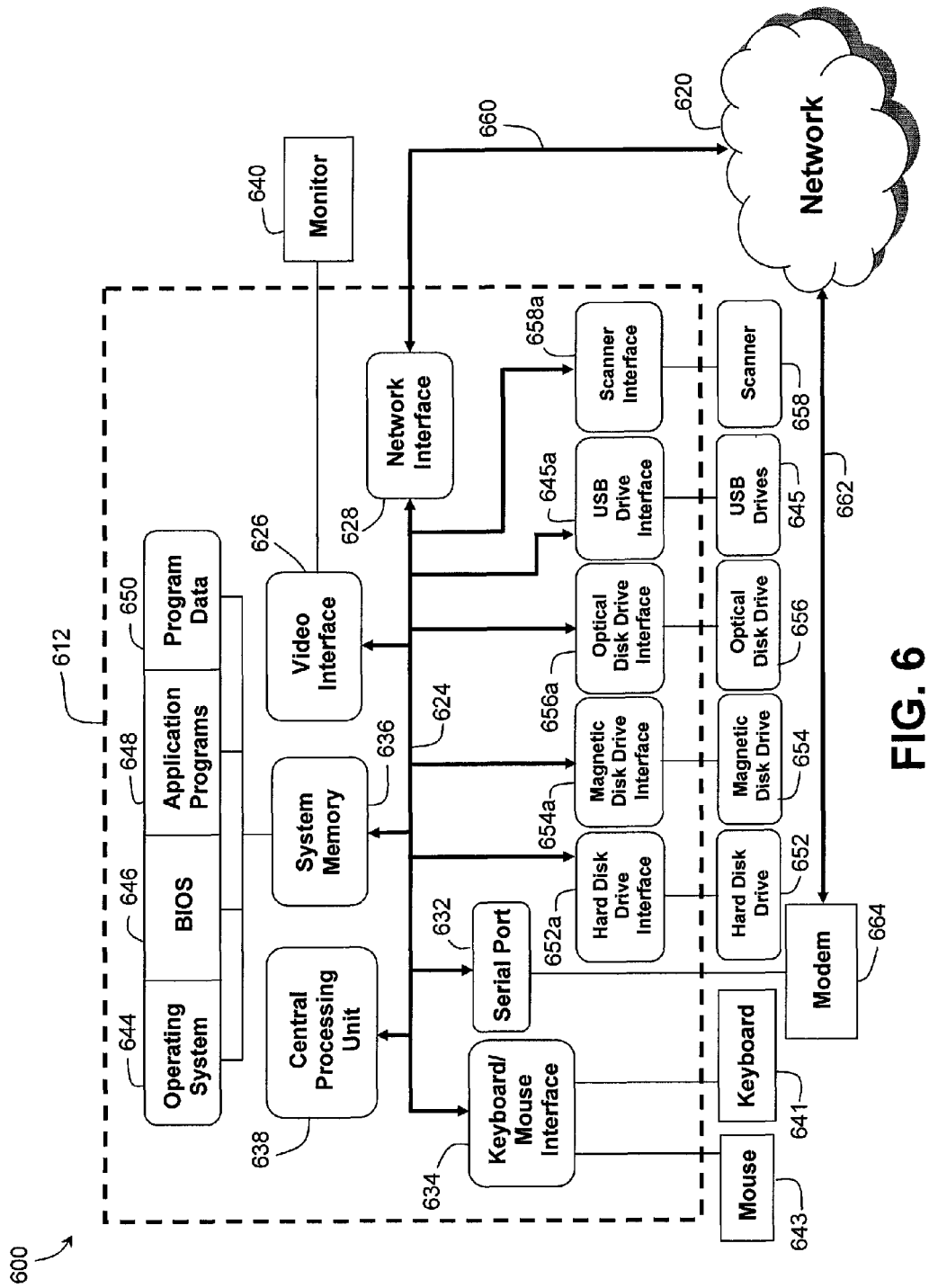
FIG. 6 is a block diagram generally illustrating a computing environment in which the invention may be implemented.

FIG. 6 shows an exemplary computing environment 600 that can be utilized through programming to implement any of the processing thus far described. The computing environment 600 may comprise a computer 612 including a system bus 624 that couples a video interface 626, network interface 628, one or more serial ports 632, a keyboard/mouse interface 634, and a system memory 636 to a Central Processing Unit (CPU) 638. Computer 612 may also include a Graphics Processing Unit (GPU) or one or more other special or general purpose processing units. A monitor or display 640 is connected to bus 624 by video interface 626 and provides the user with a graphical user interface to view, edit, and otherwise manipulate digital images. The graphical user interface allows the user to enter commands and information into computer 612 using a keyboard 641 and a user interface selection device 643, such as a mouse or other pointing device. Keyboard 641 and user interface selection device are connected to bus 624 through keyboard/mouse interface 634. The display 640 and user interface selection device 643 are used in combination to form the graphical user interface which allows the user to implement at least a portion of the present invention. Other peripheral devices may be connected to computer 612 through serial port 632 or universal serial bus (USB) drives 645 to transfer information to and from computer 612. For example, CT scanners, X-ray devices and the like may be connected to computer 612 through serial port 632 or USB drives 645 so that data representative of a digitally represented still image or video may be downloaded to system memory 636 or another memory storage device associated with computer 612 to enable processes and functions in accordance with the present invention.

The system memory 636 is also connected to bus 624 and may include read only memory (ROM), random access memory (RAM), an operating system 644, a basic input/output system (BIOS) 646, application programs 648 and program data 650. The computer 612 may further include a hard disk drive 652 for reading from and writing to a hard disk, a magnetic disk drive 654 for reading from and writing to a removable magnetic disk (e.g., floppy disk), and an optical disk drive 656 for reading from and writing to a removable optical disk (e.g., CD ROM or other optical media). The computer 612 may also include USB drives 645 and other types of drives for reading from and writing to flash memory devices (e.g., compact flash, memory stick/PRO and DUO, SD card, multimedia card, smart media card), and a scanner 658 for scanning items such as digital images to be downloaded to computer 612. A hard disk interface 652a, magnetic disk drive interface 654a, an optical drive interface 656a, a USB drive interface 645a, and a scanner interface 658a operate to connect bus 624 to hard disk drive 652, magnetic disk drive 654, optical disk drive 656, USB drive 645 and a scanner 658, respectively. Each of these drive components and their associated computer-readable media may provide computer 612 with non-volatile storage of computer-readable instruction, program modules, data structures, application programs, an operating system, and other data for the computer 612. In addition, it will be understood that computer 612 may also utilize other types of computer-readable media in addition to those types set forth herein, such as digital video disks, random access memory, read only memory, other types of flash memory cards, magnetic cassettes, and the like.

Computer 612 may operate in a networked environment using logical connections with image capture devices such as MRI, CT scanners, Ultrasound, Positron Emission Tomography (PET) or X-Ray devices. Network interface 628 provides a communication path 660 between bus 624 and network 620, which allows images to be communicated through network 620 from any of the previously identified imaging devices, and optionally saved in a memory, to the computer 612. This type of logical network connection is commonly used in conjunction with a local area network. Images may also be communicated from bus 624 through a communication path 662 to network 620 using serial port 632 and a modem 664. Using a modem connection between the computer 612 and imaging devices may be used in conjunction with a wide area network or the Internet. It will be appreciated that the network connections shown herein are merely exemplary, and it is within the scope of the present invention to use other types of network connections between computer 612 and imaging devices including both wired and wireless connections.

The present invention provides a useful, novel and non-obvious means to utilize radiological domain ontology to validate, identify and classify localized radiological information. Additionally, the present invention provides a tool that may be utilized by other applications or systems as a building block for further information processing.

From the foregoing, it will be seen that this invention is one well adapted to attain all the ends and objectives hereinabove set forth together with other advantages which are obvious and which are inherent to the method and apparatus. It will be understood that certain features and sub-combinations are of utility and may be employed without reference to other features and sub-combinations. This is contemplated by and is within the scope of the claims. Since many possible embodiments of the invention may be made without departing from the scope thereof, it is also to be understood that all matters herein set forth or shown in the accompanying drawings are to be interpreted as illustrative and not limiting.

The constructions described above and illustrated in the drawings are presented by way of example only and are not intended to limit the concepts and principles of the present invention. As used herein, the terms "having" and/or "including" and other terms of inclusion are terms indicative of inclusion rather than requirement.

While the invention has been described with reference to preferred embodiments, it will be understood by those skilled in the art that various changes may be made and equivalents may be substituted for elements thereof to adapt to particular situations without departing from the scope of the invention. Therefore, it is intended that the invention not be limited to the particular embodiments disclosed, as the best mode contemplated for carrying out this invention, but that the invention will include all embodiments falling within the scope and spirit of the appended claims.

What is claimed is:

1. A method programmed for execution in a computing environment for consulting and providing localized response information from a radiological domain ontology in reference to a subject, the method comprising:
   defining one or more aspects of radiology functions as concept properties represented by a vocabulary of one or more instances of the radiological domain ontology, the radiological domain ontology declaring and fulfilling a model of radiological domain knowledge;
   wherein said model of radiological domain knowledge comprises:
      one or more findings;
      one or more finding characteristics; and
      object properties, wherein said object properties represent relationships among said findings and finding characteristics;
   employing a context that defines a set of said radiological domain knowledge and the relationships among said set of said radiological domain knowledge, to describe said subject;
   providing an informational item of interest that relates to said subject in a localized representation; and
   providing a localization ontology, said localization ontology comprising:
      localization language references;
      localization labels for said findings, finding characteristics and object properties; and
      references to said radiological domain ontology;
      wherein a localized representation of said informational item of interest is identified in said localization language reference and the corresponding localization labels are identified and utilized to consult said radiological domain ontology to validate that said localized informational item of interest is radiological and resides in said radiological domain knowledge, wherein a definitive concept of said localized informational item of interest is identified from within said radiological domain knowledge, and wherein said localized informational item of interest is classified to provide said localized response regarding the subject.

2. The method of claim 1 wherein said classifying of localized informational item of interest identifies or defines said localized informational item of interest as one of a finding or a finding characteristic.

3. The method of claim 1 wherein the said provided response information from said radiological domain ontology is a list of said localization labels for all of said findings for said model of radiological domain knowledge.

4. The method of claim 3 wherein the provided response information from said radiological domain ontology is a list of all of said localization labels for all of said finding characteristics that apply to a given finding of claim 3.

5. The method of claim 1 wherein the provided response information from said radiological domain ontology is a list of all of said localization labels for all of said finding characteristics for said model of radiological domain knowledge.

6. The method of claim 1 further comprising validating that said localized informational item of interest is within a specific radiological context.

7. The method of claim 1 further comprising, providing a list of containers and container items, wherein a container is a characteristic concept and container items are individual finding characteristics that have applicability to a user interface for a given radiological finding concept.

8. The method of claim 1 wherein said localized information item of interest is provided in Spanish by a radiologist during the process of analyzing a patient X-ray.

9. A method programmed for execution in a computing environment for identifying, validating and classifying one or more localized radiological informational items, utilizing a localization ontology to localize a radiological domain ontology, the method comprising:
   receiving said localized radiological informational items;
   defining one or more aspects of radiology functions as concept properties represented by a vocabulary of one or more instances of said radiological domain ontology, said radiological domain ontology declaring and fulfilling a model of radiological domain knowledge
   providing localization labels for said concept properties and said vocabulary of one or more instances of said radiological domain ontology;
   accessing said localization labels to define said localized radiological informational item in said radiological domain knowledge;
   wherein said localized radiological informational items may be validated as residing in said radiological domain knowledge, identified as a definitive concept within said radiological domain knowledge, and classified within said radiological domain knowledge;
   wherein said radiological domain knowledge comprises:
      one or more findings;
      one or more finding characteristics; and
      object properties, wherein said object properties represent relationships among said findings and finding characteristics.

10. A method programmed in a computing environment for providing localized consultation of a single radiological domain ontology the method comprising:
- defining classes, properties and instances of known concepts in the radiological domain ontology in a first language;
- defining at least one default localization label for each of said classes, properties and instances in each of said first language and a second language; and
- providing a translation matching module for correlating one or more labels of said first language to one or more labels of said second language;
- whereby the radiological domain ontology may be consulted utilizing an informational item in said second language and response is provided back in said second language.

11. A computing system for identifying, validating and classifying one or more radiological informational items, utilizing a radiological domain ontology in reference to a subject comprising:
- a definition of one or more aspects of radiology functions as concept properties represented by a vocabulary of one or more instances of the radiological domain ontology, the radiological domain ontology declaring and fulfilling a model of radiological domain knowledge;
- means for receiving an informational item of interest that relates to said subject, in a localized representation;
- a context that defines a set of said radiological domain knowledge and the relationships among said set of said radiological domain knowledge to describe said subject;
- wherein said domain knowledge comprises:
  - one or more findings;
  - one or more finding characteristics; and
  - object properties,
- wherein said object properties represent relationships among said findings and finding characteristics;
- a validation module;
- an identification module;
- a classification module; and
- a localization layer ontology, said localization layer ontology comprising:
  - localization language references;
  - localization labels for said findings, finding characteristics and object properties; and
  - references to said radiological domain ontology;
  - wherein a localized representation of said informational item of interest is identified in said localization language reference and the corresponding localization labels are identified and utilized to consult the radiological domain ontology;
- wherein said validation module validates that said localized informational item of interest is radiological and resides in said set of said radiological domain knowledge, said identification module identifies a definitive concept of said localized informational item of interest from within said set of said radiological said domain knowledge, and said classification module classifies said localized informational item of interest to provide a localized response regarding the subject.

* * * * *